United States Patent
Weisbart et al.

(10) Patent No.: US 8,333,756 B2
(45) Date of Patent: *Dec. 18, 2012

(54) SCALAR LASER THERAPY APPARATUS

(76) Inventors: Paul Weisbart, Haiku, HI (US); Lillie Weisbart, Haiku, HI (US)

( * ) Notice: Subject to any disclaimer, the term of this patent is extended or adjusted under 35 U.S.C. 154(b) by 125 days.

This patent is subject to a terminal disclaimer.

(21) Appl. No.: 13/018,893

(22) Filed: Feb. 1, 2011

(65) Prior Publication Data

US 2011/0172747 A1    Jul. 14, 2011

Related U.S. Application Data

(63) Continuation-in-part of application No. 12/258,082, filed on Oct. 24, 2008, now Pat. No. 8,236,037.

(60) Provisional application No. 60/982,294, filed on Oct. 24, 2007.

(51) Int. Cl.
*A61N 5/067* (2006.01)

(52) U.S. Cl. ............................ 606/9; 607/88; 607/89

(58) Field of Classification Search ... 606/9; 607/88–91
See application file for complete search history.

(56) References Cited

U.S. PATENT DOCUMENTS

| | | |
|---|---|---|
| 4,649,935 A | 3/1987 | Charmillot et al. |
| 4,765,322 A | 8/1988 | Charmillot et al. |
| 4,930,504 A | 6/1990 | Diamantopoulos et al. |
| 4,951,663 A | 8/1990 | L'Esperance, Jr. |
| 5,358,503 A | 10/1994 | Bertwell et al. |
| 5,464,436 A | 11/1995 | Smith |
| 5,549,660 A | 8/1996 | Mendes et al. |
| 5,616,140 A | 4/1997 | Prescott |
| 5,755,752 A | 5/1998 | Segal |
| 5,800,479 A | 9/1998 | Thiberg |
| 5,830,211 A | 11/1998 | Santana et al. |
| 6,019,482 A | 2/2000 | Everett |
| 6,187,029 B1 | 2/2001 | Shapiro et al. |
| 6,443,978 B1 | 9/2002 | Zharov |
| 6,454,791 B1 | 9/2002 | Prescott |
| 6,602,275 B1 | 8/2003 | Sullivan |
| 6,702,837 B2 | 3/2004 | Gutwein |
| 6,872,221 B2 | 3/2005 | Lytle |

(Continued)

OTHER PUBLICATIONS

Final U.S. Office Action in related U.S. Appl. No. 12/258,082; dated Apr. 13, 2012.

(Continued)

*Primary Examiner* — Ahmed Farah
*Assistant Examiner* — Jeffrey Lipitz
(74) *Attorney, Agent, or Firm* — Banner & Witcoff, Ltd.

(57) ABSTRACT

There is disclosed a new low-level laser therapy apparatus and method of treating tissue. The invention includes a laser system that uses laser diodes and/or alternatively light emitting diodes (LED's), or both, and a digital interface that gives the operator the ability to generate sine waves or scalar waves as opposed to the simple on/off square waves. The invention also enables the operator to modulate not only the frequency, but also other wave characteristics such as the amplitude and phase. In one aspect, the invention involves modulating the phase relationship between multiple waves by taking one channel or wave which is pulsed through the laser system and then running a second channel or wave in relationship to the first channel, thereby creating a phased relationship, which has been discovered to provide a therapeutic and quantum healing effect on tissue. In one exemplary embodiment, the laser system of the invention may have a phase relationship of approximately 180 degrees which provides a beneficial therapeutic and quantum healing effect and, in particular, neutralizes or deletes cellular memory.

21 Claims, 4 Drawing Sheets

U.S. PATENT DOCUMENTS

2002/0198575 A1  12/2002  Sullivan
2004/0030370 A1  2/2004   Lytle
2008/0183161 A1  7/2008   Walneck et al.
2009/0112296 A1  4/2009   Weisbart et al.
2009/0227996 A1  9/2009   Powell et al.

OTHER PUBLICATIONS

International Search Report in corresponding PCT application No. (PCT/US2011/023597) mailed Oct. 24, 2011.
Canadian Office Action in related Canadian application No. 2,772,404; dated Aug. 21, 2012.

SCALAR LASER THERAPY APPARATUS

CROSS-REFERENCE TO RELATED APPLICATION

This Continuation-in-Part Application claims benefit to U.S. application Ser. No. 12/258,082, filed Oct. 24, 2008, which claims benefit to U.S. Provisional Application Ser. No. 60/982,294, filed Oct. 24, 2007.

FIELD OF THE INVENTION

The present invention relates generally to lasers for the treatment of human tissue and, more particularly, to low level lasers and light emitting diodes (LED's) that are used to provide a therapeutic and quantum effect to treat human tissue for health, rejuvenation and wellness, and the deletion of cellular memory.

BACKGROUND OF THE INVENTION

It is known that lasers and LED'S may be used to deliver energy to targeted tissue to aid in the repair of tissue damage. The lasers and LED's may also be used to provide beneficial therapeutic effect in the treatment of neurological and soft tissue conditions. More specifically, the lasers and LED's deliver energy to targeted tissue, penetrating the layers of skin to reach internal tissues to produce a specific, non-thermal photochemical effect at the cellular level. This type of therapy is non-invasive and avoids the potential side effects of drug therapy.

There remains, however, a need in the art for better laser therapy treatment. The present invention provides such improved treatment and is directed to a new low-level laser therapy apparatus and method of treating tissue.

SUMMARY OF THE INVENTION

The following presents a general summary of aspects of the invention in order to provide a basic understanding of the invention and various features of it. This summary is not intended to limit the scope of the invention in any way, but simply provides a general overview and context for the more detailed description that follows.

The present invention is directed to a hand-held laser system that uses laser diodes and/or alternatively LED's, or both, to provide energy to targeted tissue to provide a beneficial therapeutic and quantum healing effect, and to neutralize or delete cellular memory. The hand-held laser system includes a digital interface that gives the operator the ability to generate sine waves or scalar waves at a particular frequency, as opposed to the simple on/off square waves that non-digital systems use. The laser system also enables the operator to modulate not only the frequency, but also other wave characteristics such as the amplitude and phase. One aspect of the invention involves modulating the phase relationship between multiple waves in the laser system. In other words, the invention takes one channel or wave (frequency) which is pulsed through the laser and then runs a second channel or wave in relationship to the first channel. This is referred to as the phase relationship of the waves and is measured between 0 and 360. It has been discovered that the laser system of the invention having a phase relationship between waves, such as sine and scalar waves, has a therapeutic and quantum healing effect on tissue. In one exemplary embodiment, it has been discovered that the laser system of the invention having a phase relationship of approximately 180 degrees provides a desired therapeutic and quantum healing effect and, in particular, neutralizes or deletes cellular memory.

Other features and advantages of the invention will become apparent to those skilled in the art upon review of the following detailed description, claims and drawings in which like numerals are used to designate like features.

Figure 1:
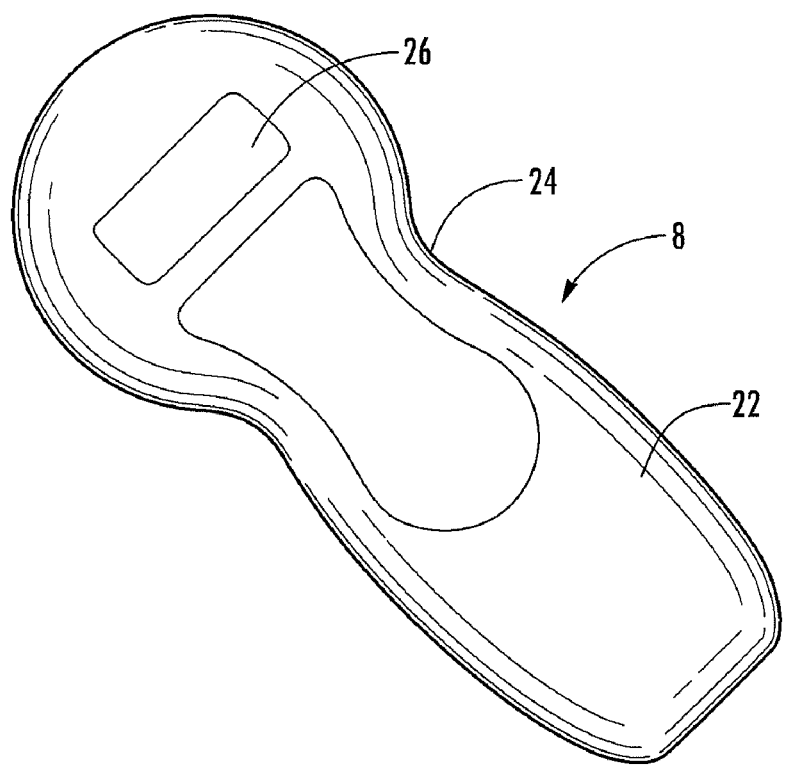
FIG. 1 is a top plan view of an exemplary embodiment of a laser therapy apparatus of the present invention.

Before the embodiments of the invention are explained in detail, it is to be understood that the invention is not limited in its application to the details of construction and the arrangement of the components set forth in the following description or illustrated in the drawings. The invention is capable of other embodiments and of being practiced or being carried out in various ways. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof.

DETAILED DESCRIPTION OF THE EMBODIMENTS

Figure 2:
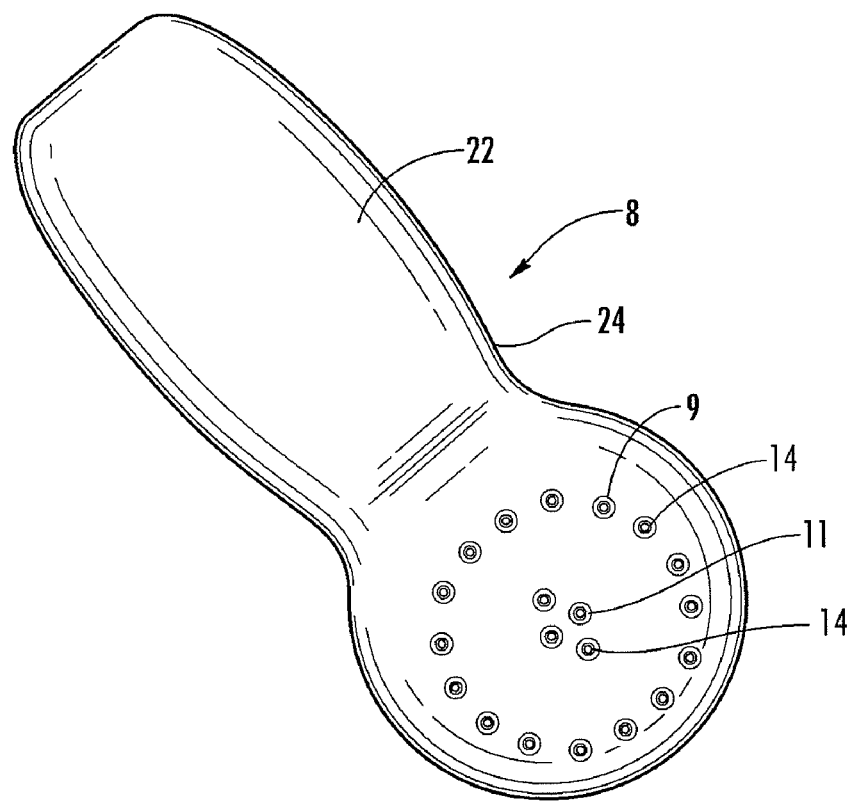
FIG. 2 is a bottom view of the laser apparatus of FIG. 1, illustrating an exemplary laser diode and LED pattern.

Referring to FIGS. 1 and 2, there is shown an exemplary hand-held, battery-powered laser therapy apparatus 8 of the invention which includes a plurality of laser diodes and/or LED's emitting light at particular wavelengths for the purpose of providing energy to the human body in therapeutic applications. The exemplary therapy apparatus 8 may include on one side a plurality of laser diodes and/or LED's 14 arranged in a particular pattern that emit visible and near-infrared radiation to provide therapeutic and quantum healing effect and to neutralize or delete cellular memory. This is accomplished by modulating the phase relationship between multiple waves in the laser system. It has been determined that the laser system of the invention having a phase relationship between waves, such as sine and scalar waves, has a desired therapeutic and quantum healing effect on tissue. As further explained below, a laser system having a phase relationship of approximately 180 degrees provides this desired therapeutic and healing effect, and neutralizes or deletes cellular memory.

Figure 3:
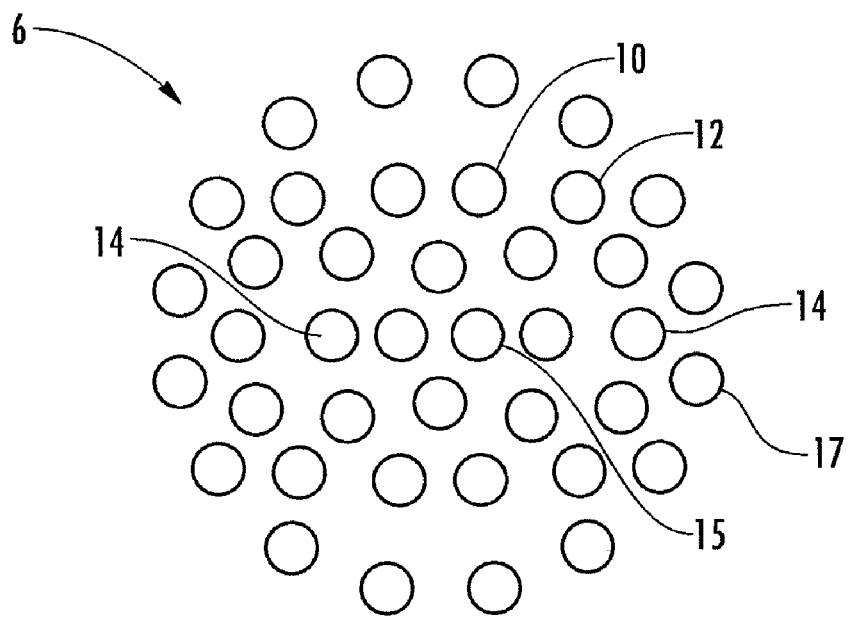
FIG. 3 is a schematic of an alternative laser diode and LED pattern.

In one embodiment, and as shown in FIG. 3, the laser therapy apparatus 8 may include at least two tracks 10, 12 of spaced-apart laser diodes and/or LED'S 14 with each track having approximately ten laser diodes. The two tracks 10, 12 may be configured in a concentric pattern, i.e., one track inside the other, or other suitable patterns. The number of diodes 14 may vary depending on the desired application. In one embodiment of the invention, the phase relationship between the tracks 10, 12 may be set to approximately 180 degrees, or set to any other suitable phase relationship. By using this configuration of diodes with the same frequencies being pulsed through each track, but with different phase relationships between the tracks, studies have shown that the laser therapy apparatus 8 will provide a very unique and beneficial healing and rejuvenation effect, and the deletion of cellular memory.

In an exemplary embodiment, the diodes 14 may include one or more red (650 nm) laser diodes each having a power of 5 mW. The diodes 14 may also include one or more infrared (780 nm) laser diodes each having a power of 5 mW, or may include one or more 405 nm laser diodes each having a power of 100 mW. Additionally, the diodes 14 may include one or more violet (420 nm) laser diodes or one or more violet LED's each having a power of 1000 mcd. In an exemplary embodiment, the diodes may include laser diodes between 400 nm and 470 nm wavelengths. It should be understood that other diodes having other powers are possible and may be used with the laser apparatus of the invention. Laser diodes in this wavelength range have not previously been a viable option to provide a beneficial therapeutic and quantum healing effect, and to neutralize or delete cellular memory. It has been determined that laser diodes in this wavelength range result in wellness enhancing benefits for rejuvenation, alchemy, anti aging, and the activation of key enzymes. In yet another alternative embodiment, the apparatus may use all violet laser diodes.

The apparatus 8 may have a frequency range from 1 Hz to 20,000 Hz sine wave, and 40 Hz square wave. In an alternative embodiment, the laser apparatus 8 may have specific frequencies between 1 and 40,000 Hz that are pulsed through the laser apparatus. Using specific frequencies between 1 Hz and 40,000 Hz has been shown to provide therapeutic value of fine tuning the laser energy to stimulate and induce different therapeutic effects such as the relaxation of tissue, stimulating circulation, detoxification, and rejuvenation. The diodes 14 may be mounted to or in the apparatus 8 and may be configured such that laser or LED beams emitted therefrom travel parallel to each other, or intersect at a short distance away from the apparatus 8.

In an alternative embodiment, the apparatus 8 may include one laser diode surrounded by four LED's. With this embodiment, the laser diode may be one higher power than the four LED's. In this embodiment, the laser diode may define one circuit, while the surrounding four LED's define a separate circuit. In an alternative aspect, there may be up to five or more LED/laser clusters arranged on the apparatus 8. Each cluster will have its own control capability independent of the others. In another alternative embodiment, four circuits comprised of laser diodes or LED's may be used with the laser apparatus. In this embodiment, referring to FIG. 4a, there is a first circuit 50, a second circuit 52, a third circuit 54, and a fourth outer circuit 56 of diodes placed in a concentric pattern of circuits. The concentric pattern of circuits may define a circular, elliptical or other pattern of circuits that surround each other. In this embodiment, the first circuit 40 and third circuit 44 are woven together into a first track, the second circuit 42 and fourth circuit 46 are woven together into a second track. The first track has a first wave phase and the second track has a second wave phase, wherein the second wave phase of the second track has approximately a 180 phase difference relative to the first wave phase of the first track. With this embodiment, the laser therapy apparatus will provide a very unique and beneficial healing and rejuvenation effect, and the deletion of cellular memory. It should be understood by those skilled in the art that numerous combinations or laser diodes and LED's are possible with the teachings of the invention, as further illustrated below.

In one embodiment, the apparatus 8 may define a body portion 22 that may be fabricated, for example, from a molded plastic material, such as ABS/poly blend. The body portion 22 may define a contoured grip portion 24 that permits the operator to more easily handle the laser apparatus. The body portion 22 will contain the circuitry that controls the operation of the laser apparatus 8 and the diodes 14. The body portion also contains a battery, not shown, such as a lithium ion rechargeable battery. The body portion 22 may further contain charging circuitry to allow a simple external power source to be used for charging.

In an exemplary embodiment, and as shown in FIG. 1, the laser apparatus 8 may include on top of the unit a display 26, such as an LCD character display and keypad readout, to allow the user to select from many therapy modes. Additionally, light intensity, flash frequency, and flash duration may be adjusted for each mode. The display may also provide such information as projected time of operation remaining based on battery capacity, and may provide a visual alarm indicating the number of minutes remaining when capacity runs low. The display also enables the operator to modulate not only the frequency, but also other wave characteristics such as the amplitude and phase.

Referring to FIG. 2, there is shown an alternative arrangement of the plurality of spaced apart laser diodes and/or LED's 14 positioned in a concentric pattern on the body portion 22. As depicted, a first outer ring 9 of diodes 14 may be positioned near the periphery of the body portion and define one track, and a second diamond-shaped pattern 11 of diodes 14 may be positioned near the center of the body portion and define a second track. As indicated above, any number of combinations of laser diodes and/or LED's 14 may be used as part of the outer ring 9 or the diamond-shaped pattern 11. In the embodiment depicted in FIG. 2, the first outer ring 9 may include LED's, and the second diamond-shaped pattern 11 may include laser diodes.

Referring to FIG. 3, in another aspect of the invention, and as explained above, the laser apparatus 8 may have a pattern 6 that includes at least two tracks 10, 12 of spaced apart laser diodes and/or LED'S 14. The pattern may also include an inner diamond-shape arrangement 15 of diodes 14 and an outer ring 17 of diodes 14, each defining their own respective track. The two tracks 10, 12 may be configured in a concentric pattern, or other suitable patterns. The phase relationship between these two tracks may be set to approximately 180 degrees to provide the desired therapeutic effect. By using this configuration of diodes with the same frequencies being pulsed through each track, but with different phase relationships between the tracks, the laser system will provide a beneficial healing effect, and will result in the deletion of cellular memory. Each track will have its own circuitry for control capability independent of the other track of diodes. In the embodiment of FIG. 3, the tracks 10, 12 will include laser diodes and the inner diamond-shaped arrangement 15 and outer ring 17 will include LED's, all being arranged concentrically with each other and all on their own respective tracks. It should be understood that this diode configuration and the particular diodes used therein is merely exemplary of the numerous possible laser diode and/or LED patterns.

Figure 4:
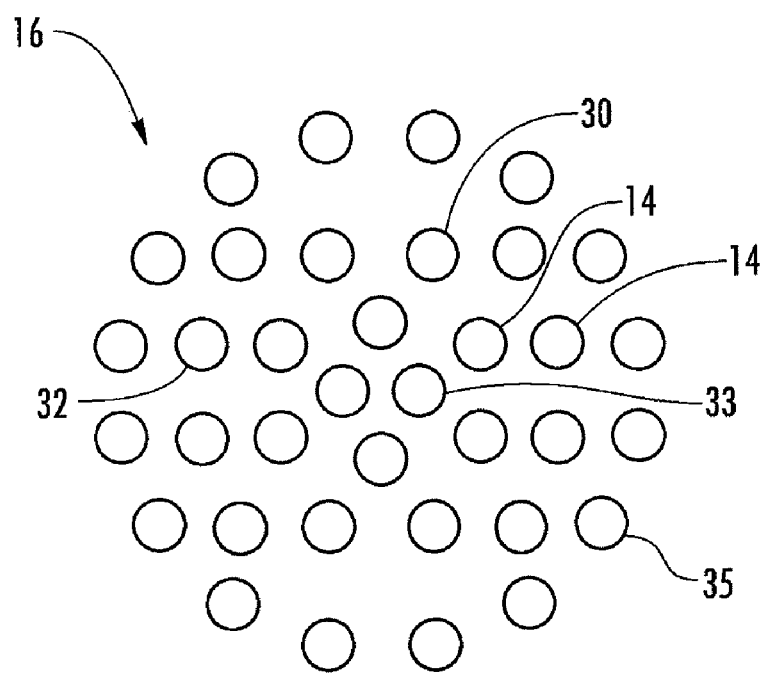
FIG. 4 is a schematic of another alternative laser diode and LED pattern.
Figure 4A:
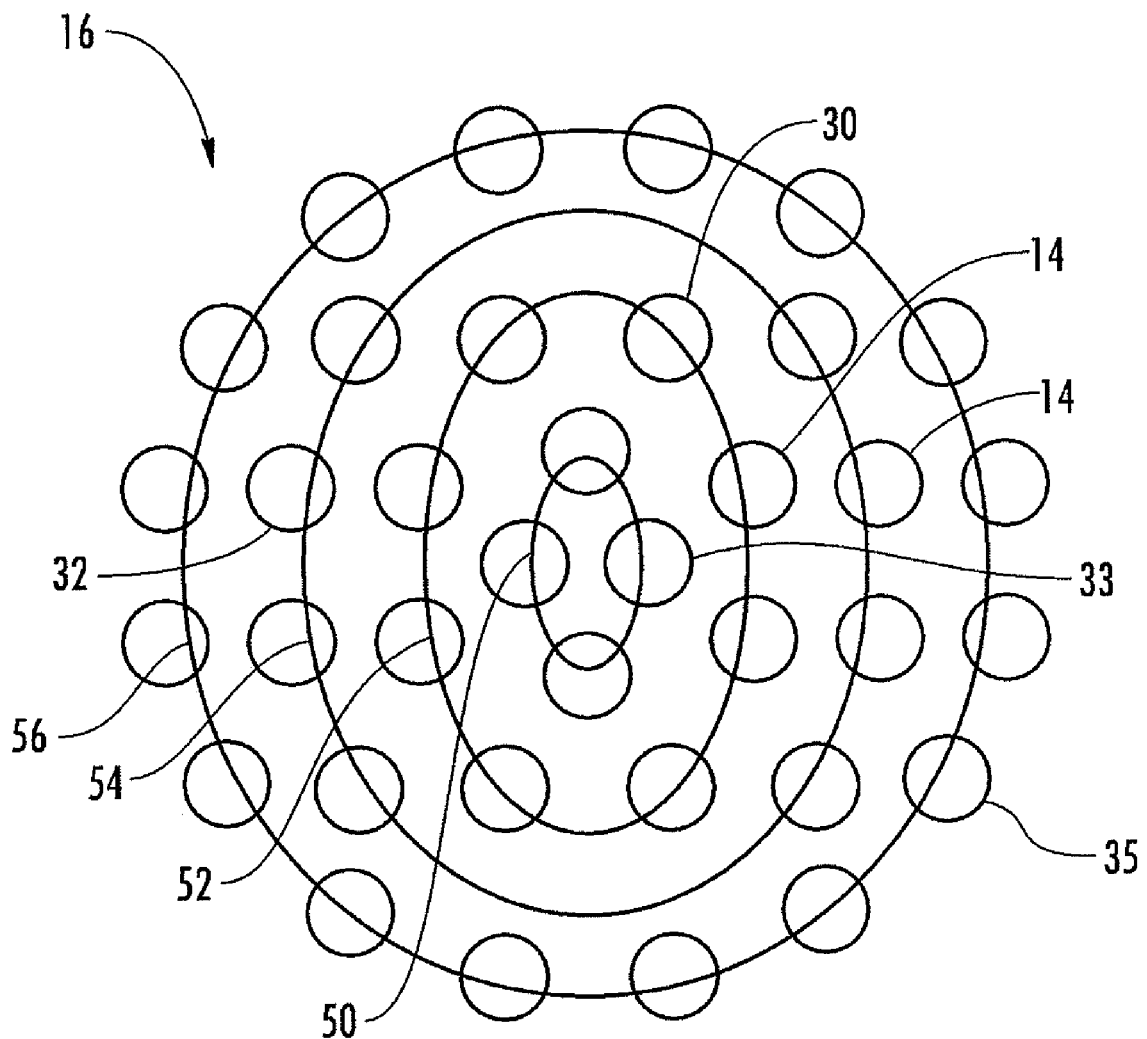
FIG. 4a is a schematic of another alternative laser diode and LED pattern.

Referring to FIG. 4, in yet another aspect of the invention, the laser apparatus 8 may have a pattern 16 that includes two tracks 30, 32 of spaced apart laser diodes and/or LED'S 14. In this embodiment, each track may have approximately eight laser diodes. The pattern 16 may also have an inner diamond-shaped arrangement 33 of diodes defining a track and an outer ring 35 of diodes also defining a track. The two tracks 30, 32 may be configured in a concentric pattern, or other suitable patterns. Similar to the embodiment of FIG. 3, the phase relationship between these two tracks may be set to approximately 180 degrees, or set to any other suitable phase relationship. Again, by using this configuration of diodes with the same frequencies being pulsed through each track, but with different phase relationships between the tracks, the laser system will provide a beneficial healing effect, and the deletion of cellular memory. Also again, each track of diodes will have its own circuitry for control capability independent of the other track of diodes. In the embodiment of FIG. 4, the tracks 30, 32 will include laser diodes, and the inner diamond-shaped arrangement 33 and outer ring 35 will include LED's. Again, the particular laser diode and/or LED's used with the depicted pattern 16 may vary.

Figure 5:
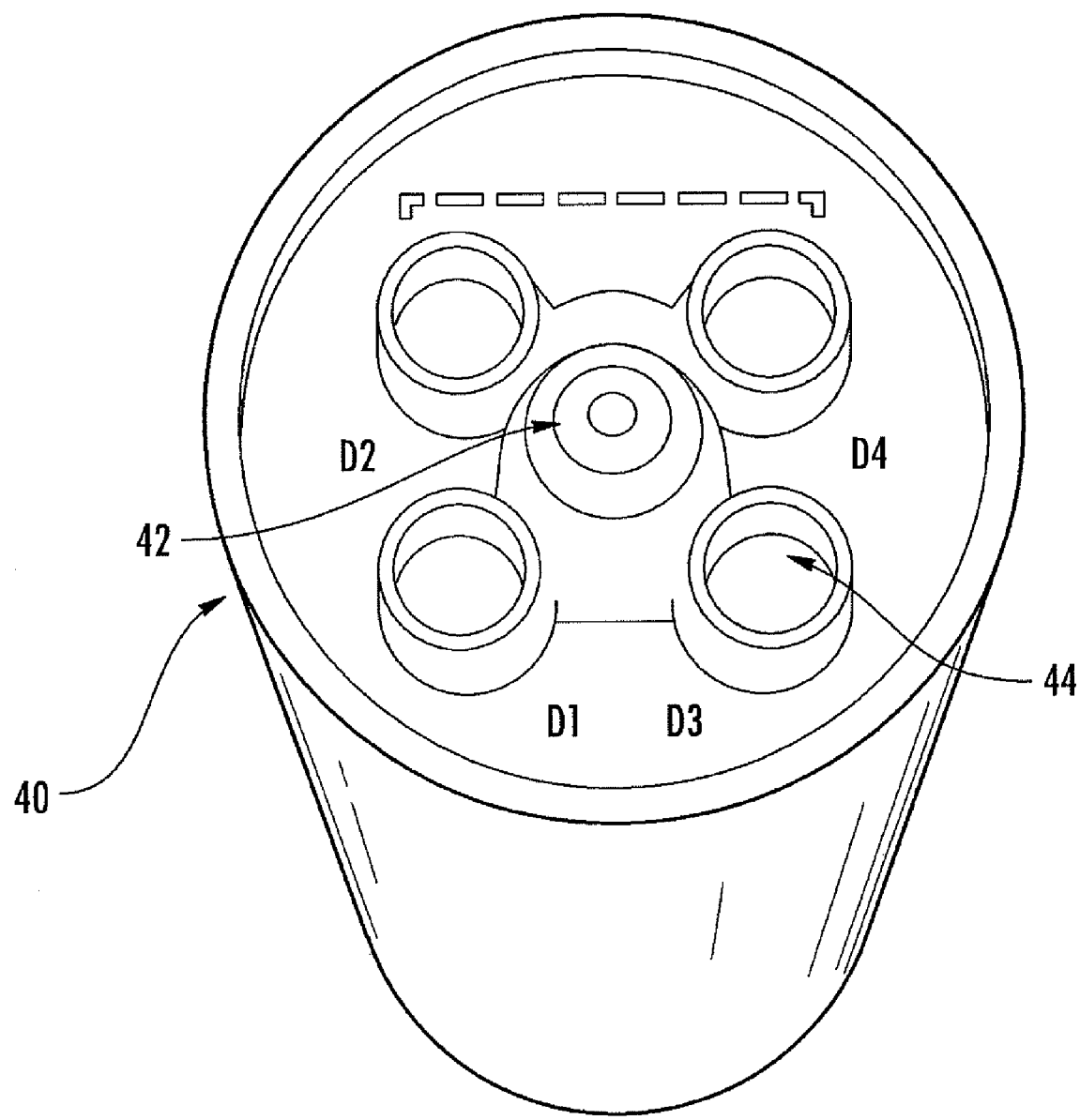
FIG. 5 is a top view of an exemplary laser therapy probe of the present invention.

In an alternative aspect, a higher power laser probe 40 (FIG. 5) may be coupled to the laser therapy apparatus 8 to provide precision therapy applications. This laser probe may be an accessory attachment to the apparatus 8 and may be powered from the apparatus 8. Referring to FIG. 5, the laser probe 40 may define an elongated body that may be hand-held. The probe 40 may include any number of laser diodes 42 and/or LED's 44. In an exemplary embodiment, the probe 40 may define a diode pattern that includes a laser diode 42 defining a first track surrounded by four LED's 44 which define a second track. It should be understood by those skilled in the art that other diode patterns are possible. In one embodiment, the probe diodes may include one or more red (650 nm) laser diodes each having a power of 100 mW. The diodes may also include one or more infrared (780 nm) laser diodes each having a power of 100 mW. Also, the diodes may include one or more 405 nm laser diodes each having a power of 60 mW. Additionally, the diodes may include one or more violet (420 nm) LED's. In an exemplary embodiment, the diodes may include laser diodes between 400 nm and 470 nm wavelengths. Again, the particular laser diodes and/or LED's used with the probe may vary. Similar to the laser apparatus 8, the phase relationship between the diodes used with the probe 40 may be set to approximately 180 degrees, or set to any other suitable phase relationship. Again, by using this configuration of diodes with the same frequencies being pulsed through each track, but with different phase relationships between the tracks, such as 180 degrees phase difference, the laser probe 40 will provide a beneficial healing effect, and the deletion of cellular memory. Also similar to the laser apparatus 8, each track of diodes will have its own circuitry for control capability independent of the other track of diodes.

Variations and modifications of the foregoing are within the scope of the present invention. It should be understood that the invention disclosed and defined herein extends to all alternative combinations of two or more of the individual features mentioned or evident from the text and/or drawings. All of these different combinations constitute various alternative aspects of the present invention. The claims are to be construed to include alternative embodiments to the extent permitted by the prior art. Various features of the invention are set forth in the following claims.

What is claimed is:

1. A laser therapy apparatus comprising:
a plurality of laser diodes and/or light emitting diodes configured on a housing body, wherein the laser diodes have a wavelength of between 400 nm and 470 nm, control circuitry to control the operation of the laser diodes and/or light emitting diodes, the plurality of laser diodes and/or light emitting diodes defining a first track and a second track, the control circuitry digitally controlling the first track of diodes to provide a first sine wave having a first phase, the control circuitry digitally controlling the second track of diodes to provide a second sine wave having a second phase, the first track of diodes having an approximately 180 degree phase difference relative to the second track of diodes to provide therapeutic effect.

2. The laser therapy apparatus of claim 1, further comprising laser diodes that have a wavelength of 650 nm or 780 nm.

3. The laser therapy apparatus of claim 2, wherein the first and second tracks are arranged concentrically.

4. The laser therapy apparatus of claim 3, further comprising a plurality of light emitting diodes and/or laser diodes defining a diamond shape and concentrically positioned within the first track.

5. The laser therapy apparatus of claim 4, wherein the plurality of light emitting diodes and/or laser diodes defining a diamond shape have a wavelength of between 400 and 470 nm.

6. The laser therapy apparatus of claim 5, wherein the first track, second track and the plurality of light emitting diodes and/or laser diodes defining a diamond shape are all arranged concentrically.

7. The laser therapy apparatus of claim 6, wherein the frequencies of the diodes of the first and second tracks are the same, while the phase relationships of the diodes between the tracks are different.

8. The laser therapy apparatus of claim 6, further comprising a ring of light emitting diodes and/or laser diodes configured around the first track and the second track.

9. The laser therapy apparatus of claim 1, further comprising a laser probe coupled to the housing body, the laser probe including a plurality of laser diodes and/or light emitting diodes configured on the probe.

10. The laser therapy apparatus of claim 9 wherein the plurality of probe laser diodes and/or light emitting diodes have a wavelength of between 400 nm and 470 nm.

11. The laser therapy apparatus of claim 9, wherein the plurality of probe laser diodes and/or light emitting diodes include a first laser diode defining a first phase surrounded by multiple light emitting diodes defining a second phase, and wherein the first phase is approximately 180 degrees different than the second phase to provide therapeutic effect.

12. The laser therapy apparatus of claim 1, further comprising an LCD display configured on the housing body.

13. The laser therapy apparatus of claim 1, wherein specific frequencies between 1 and 40,000 Hz are pulsed through the laser apparatus.

14. A laser therapy apparatus comprising:
a plurality of laser diodes and/or light emitting diodes configured on a housing body,
control circuitry to control the operation of the laser diodes and/or light emitting diodes,
wherein the plurality of laser diodes and/or light emitting diodes defining a first track and a second track,
wherein the first track of diodes defines a first circuit and a third circuit,
wherein second track of diodes defines a second circuit and a fourth circuit,
wherein the control circuitry digitally controls the first track of diodes to provide a first sine waveform having a first wave phase, and digitally controls the second track of diodes to provide a second sine waveform having a second wave phase,
wherein the first track of diodes having an approximately 180 degree phase difference relative to the second track of diodes to provide therapeutic effect.

15. The laser therapy apparatus of claim 14, wherein specific frequencies between 1 and 40,000 Hz are pulsed through the laser apparatus.

16. The laser therapy apparatus of claim 15, wherein the first and second tracks are arranged concentrically.

17. The laser therapy apparatus of claim 15, further comprising a plurality of light emitting diodes and/or laser diodes defining a diamond shape and concentrically positioned within the first track.

18. The laser therapy apparatus of claim 15, wherein the plurality of laser diodes and/or light emitting diodes have a wavelength of between 400 nm and 470 nm.

19. The laser therapy apparatus of claim 14, further comprising a laser probe coupled to the housing body, the laser probe including a plurality of laser diodes and/or light emitting diodes configured on the probe.

20. The laser therapy apparatus of claim 19, wherein the plurality of probe laser diodes and/or light emitting diodes include a first laser diode defining a first phase surrounded by multiple light emitting diodes defining a second phase, and wherein the first phase is approximately 180 degrees different than the second phase to provide therapeutic effect.

21. A laser therapy apparatus comprising:
a plurality of laser diodes and/or light emitting diodes configured on a housing body, a digital interface to control the operation of the laser diodes and/or light emitting diodes, the plurality of laser diodes and/or light emitting diodes defining a first track and a second track, the digital interface controlling the first track of diodes to provide a first sine waveform having a first wave phase, and controlling the second track of diodes to provide a second sine waveform having a second wave phase, the first track of diodes having a phase difference relative to the second track of diodes to provide therapeutic effect, wherein specific frequencies between 1 and 40,000 Hz are pulsed through the laser apparatus.

* * * * *